US006447296B2

(12) United States Patent
Worthington (10) Patent No.: US 6,447,296 B2
(45) Date of Patent: Sep. 10, 2002

(54) QUADRANT AND ANTERIOR DENTAL SHELLS AND METHOD OF MAKING A MULTI-TOOTH CROWN OR BRIDGE

(75) Inventor: Mark L. Worthington, Eugene, OR (US)

(73) Assignee: Directcrown, LLC, Eugene, OR (US)

( * ) Notice: Subject to any disclaimer, the term of this patent is extended or adjusted under 35 U.S.C. 154(b) by 0 days.

(21) Appl. No.: 09/808,700

(22) Filed: Mar. 14, 2001

Related U.S. Application Data (60) Provisional application No. 60/190,127, filed on Mar. 16, 2000.

(51) Int. Cl.[7] .................................................. A61C 5/08
(52) U.S. Cl. ...................................... 433/183; 433/218
(58) Field of Search ................................ 433/218, 219, 433/191, 81, 183, 180

(56) References Cited

U.S. PATENT DOCUMENTS

| 4,015,332 A | 4/1977 | Manne |
| 4,678,435 A | 7/1987 | Long ........................... 433/218 |
| 4,710,127 A | * 12/1987 | Bellavia et al. ............. 433/215 |
| 4,778,386 A | 10/1988 | Spiry ........................... 433/45 |
| 5,458,489 A | 10/1995 | Tennyson .................... 433/181 |
| 5,803,737 A | 9/1998 | Lyalin ......................... 433/223 |
| 5,927,934 A | 7/1999 | Lin ............................. 433/218 |
| 6,068,481 A | 5/2000 | Worthington ............... 433/219 |

* cited by examiner

*Primary Examiner*—Nicholas D. Lucchesi
*Assistant Examiner*—Melba Bumgarner
(74) *Attorney, Agent, or Firm*—Marger Johnson & McCollom, P.C.

(57) ABSTRACT

A quadrant and/or anterior shell for making a bridge or multi-tooth crown includes a plurality of integrally formed shell segments. Each shell segment corresponds to a different tooth in the respective quadrant and/or anterior region. Each shell has an occlusal surface, formed on a top wall, that replicates the occlusal surface of a natural tooth. A method of forming bridges or crowns using such shells includes selecting or sectioning off an appropriate section of the shell. The selected shell section is filled with resin. The shell section is positioned over prepared teeth, and, in the case of a bridge, also over a gap in the patient's dentition. Resin extrudes from mesio-distal sides and gingival margins of the shell section to form good proximal and gingival contacts. Once the resin has set, the resin and shell section are shaped to form the final crown or bridge.

27 Claims, 3 Drawing Sheets

QUADRANT AND ANTERIOR DENTAL SHELLS AND METHOD OF MAKING A MULTI-TOOTH CROWN OR BRIDGE

RELATED APPLICATION DATA

Priority is claimed from Ser. No. 60/190,127 filed Mar 16, 2000.

BACKGROUND OF THE INVENTION

This invention relates generally to fabricating temporary and semi-permanent bridges and to temporization where multiple teeth are involved. More particularly, this invention extends the concepts for constructing and using shells for temporary and provisional crowns, as disclosed in Applicant's prior patent applications (including U.S. Pat. No. 6,068,481, U.S. Ser. No. 09/178,023 filed Oct. 23, 1998, PCT/US98/22813, and Ser. No. 60/131,817, filed Apr. 29, 1999, each herein incorporated by reference), to the creation of temporary and semi-permanent bridges and multi-tooth crowns.

Applicant's prior applications disclose flexible dimension crown shells and methods of making temporary and long-term provisional dental crowns using such shells. As noted in those applications, three primary methods have been used for fabricating temporary and provisional crowns. In a first technique, conventional prefabricated crown forms or shells, made of a metal such as aluminum or stainless steel, or of a polycarbonate such as the Ion crown forms sold by 3M Corporation, are trimmed and shaped to fit a prepared tooth. Examples of temporary crowns of this type are disclosed in U.S. Pat. No. 4,015,332 (Manne), U.S. Pat. No. 4,678,435 (Long), U.S. Pat. No. 4,778,386 (Spiry), and U.S. Pat. No. 5,458,489 (Tennyson).

A second technique calls for making an impression of the tooth before the tooth is prepared for a crown. After the impression is made, the tooth is prepared and the impression, filled with a bis-acryl material, is placed over the prepared tooth. After the bis-acryl material sets, it is removed from the dental impression, and then trimmed, polished, and seated in the mouth.

A third primary technique proceeds by placing a putty-like ball of polymethyl-methacrylate over a prepared tooth. The patient then bites down and the material begins to set. Before it completely sets, the putty-like material is removed from the tooth, trimmed and placed back on the tooth. Once the material sets, it is then trimmed again and the bite adjusted. Finally, the temporary crown is cemented to the tooth. In a variation of this technique, as disclosed in U.S. Pat. No. 5,385,469, a tubular dental form for forming a universal crown in situ is used.

Each of these techniques has various advantages and disadvantages. Using prefabricated forms, as in the first technique, for example, is fast and simple, but the fit of conventional pre-formed shells is not very good. The margins, in particular, do not fit well. Specifically, it is hard to get good proximal contact to adjacent teeth, and the contours and occlusion are not always good. Some manufacturers try to overcome these drawbacks by proliferating sizes and shapes of shells, with some selections providing as many as 80 different sizes and shapes of molars and bicuspids. Unfortunately, this attempted solution is expensive in terms of materials and also in terms of the time required for the dentist to pick the right shell.

Manne adds a degree of freedom to the first technique by providing an incisor shell that has slits in its mesio-distal sides to permit the shell to flex in the labio-lingual direction about a hinge axis located at the occlusal surface. Long also provides a degree of freedom in this technique by providing open mesio-distal sides to permit the acrylic resin filler material to protrude proximally to contact adjacent teeth. These shells, like others used in this technique, require trimming the free edges of their buccal and lingual sidewalls to ensure a good fit along the gingival margins, as well as a good occlusion. Trimming and fitting is time-consuming for the dentist and the patient.

The second technique gives good contours and bite accuracy, but making an impression is time-consuming. Furthermore, neither the strength nor the durability of temporary crowns produced by this technique are very good. Furthermore, the impression cannot be made if the patient's tooth is already broken when initially treated. The third technique, namely, free-forming a temporary crown of putty-like material, can be accurate and fairly fast compared to the other techniques, but only if performed by a skilled dentist or technician.

Another main problem with the third approach is that it is very technique-sensitive. A dental technician must be highly skilled in order to accurately carve the tooth anatomy into the tooth replacement. A still further problem with this technique is that special care must be taken to ensure that the patient's mouth is not injured by the exothermal reaction involved in curing the crown material.

All of the foregoing techniques are undesirably slow. Even the fastest of these techniques generally takes half an hour or more of work for the dentist to fit a temporary or provisional crown to a patient. Additionally, the crowns resulting from the second and third techniques are typically not very durable and are therefore not well-suited for long-term wear. Although the stainless steel shells of the first technique are very durable, it is more difficult to fit stainless steel shells to the patient and to grind the shells' occlusal surfaces to get a comfortable bite.

Applicant's prior inventions improve over each of these techniques by providing durable shells that are sized and shaped to simplify the crown forming process. In general, the technique disclosed in Applicant's earlier applications combines the best aspects of two of the conventional techniques, namely, the free-form and specially-designed shell techniques. Specifically, shells according to applicant's prior invention include an occlusal top wall, buccal and lingual sidewalls, and mesio-distal sidewalls. The occlusal surface of the top wall approximates the occlusal surface of a natural tooth. A window is provided in at least one of the mesio-distal sidewalls. A resin is used to fill the shell. The resin is shape-controlled by the shell and the windows provided therein. This shape control saves the dentist valuable time in shaping the temporary or long-term provisional crown.

The mesio-distal sidewalls of the shells can also each include a recessed area adjoining the windows that receives and retains protruding resin in proximal contact with adjacent teeth. Each recessed area preferably forms a concavity conforming to the convexity of the mesio-distal side of the respective adjacent tooth. The shells can also have short labial and lingual side walls so that no trimming of the shells themselves is needed. This, too, saves the dentist a great deal of time. The shells also give the dentist several degrees of freedom, so that most molars and bicuspids can be fitted using a limited range of sizes and shapes of shells. These shells, and the method of using them thereby offer substantial advantages over the prior art.

Despite the improvements offered by applicant's prior inventions described above, neither it, nor any of the other prior art techniques, readily facilitate the preparation of multiple crowns at the same time. They also do not address the use of shells in preparing bridges to replace missing teeth.

Prosthodontics involves the replacement of missing teeth and related mouth or jaw structures by bridges, dentures, or other artificial devices. Bridges, in particular, are prosthodontic devices used to replace one or more missing teeth as well as to restore one or more damaged teeth. Bridges typically consist of a cast member that bridges the edentulous space (gap) caused by a missing tooth or teeth. The bridge is generally supported by adjacent natural teeth, called abutment teeth.

Unfortunately, most present methods for constructing bridges are unduly time-consuming and complex. Installing a permanent bridge is generally prefaced by the construction and installation of a temporary bridge. Temporary bridges are typically necessary because the process of constructing the permanent bridge is time consuming. The temporary bridge is used to provide temporary tooth replacement while the permanent bridge is being prepared.

Even preparing and installing temporary bridges, however, is generally more complex, time consuming, and expensive than desirable. Some prior art techniques involve the creation of custom molds and impressions that are patient-specific. These techniques are expensive and burdensome because they require a large amount of dentist time. Other techniques involve prefabricated dental pontic assemblies and connectors or molds. While these techniques offer some improvement over custom-formed assemblies, they too have shortcomings.

One approach to constructing a temporary bridge using a prefabricated mold is disclosed in U.S. Pat. No. 5,803,737 ("Lyalin"). More particularly, Lyalin discloses providing multiple preformed molds for use in preparing a temporary bridge. Each preformed mold is horse-shoe shaped and comprises sixteen recesses. Each recess is formed internally to mold the external shape of a corresponding tooth. The pre-formed molds can be made in various arch shapes and tooth lengths and widths to permit selection of a mold that more closely matches a patient's dentition. Once the appropriate preformed mold is selected, a desired subsection of the mold is sectioned off from the rest of the mold and used to form the bridge.

To form the bridge, the selected mold subsection is filled with an acrylic resin and emplaced over the edentulous space and prepared abutment teeth while the resin is allowed to cure. Once set, the mold subsection and hardened resin are removed from the mouth. The cast bridge is then removed from the mold, trimmed as necessary, and then secured in the patient's dentition over the endentulous space and on top of the abutment teeth to form a temporary bridge.

Despite the improvements offered by prior art prosthodontic devices such as the Lyalin device, a need remains for a method of making temporary and semi-permanent bridges and multi-tooth crowns that is quick and accurate, that provides a good fit without substantial trimming, that is durable enough for long-term use, and that is inexpensive. Likewise, an improved bridge and multi-tooth crown shell is also desirable.

SUMMARY OF THE INVENTION

It is, therefore, an object of the present invention to simplify the fabrication, fitting, and installation of temporary and semi-permanent bridges and multi-tooth crowns.

Another object of the present invention is to make temporary and semi-permanent bridges and multi-tooth crowns that fit well and are durable enough for long-term use.

A further object is to make bridges and multi-tooth crowns that fit well but are inexpensive both in terms of materials and time taken to fit them.

The term "quadrant dentistry" is used to refer to the dental practice of restoring multiple teeth in one quadrant (i.e., lower left, lower right, upper left, or upper right) of the mouth. In general, the present invention builds on applicant's prior inventions by providing a multi-tooth shell and technique for performing quadrant dentistry. The invention is also applicable to replacing or restoring anterior teeth.

A multi-tooth shell according to the present invention is obtained by forming an integral quadrant or anterior shell including multiple single-tooth shell segments. A multi-tooth shell could also be made to include teeth from both a quadrant and an anterior region. The multi-tooth shells are formed as a series of single-tooth shell segments, wherein each segment has the external shape of a corresponding tooth and a central cavity shaped to fit loosely over a prepared tooth. A quadrant shell, for instance, can include segments corresponding to cuspids, bicuspids, and molars, that are integrally molded as a shell unit. The quadrant shell can also be fitted into a patient's mouth as an integral unit. Although the quadrant shell can be made to encompass any number of multiple teeth, e.g. two or three or more, it is preferably made to encompass four, or most preferably, five teeth.

The four-tooth quadrant shell embodiment preferably provides either two molars and two bicuspids, or one molar, two bicuspids, and a cuspid, in the order normally occurring in human dentition. The five-tooth embodiment preferably comprises one cuspid, two bicuspids, and two molars. In yet another alternative embodiment, the quadrant shell could be made to correspond to just three teeth—such as a cuspid and two bicuspids, two bicuspids and a molar, or a biscuspid and two molars.

A method for using a shell of the present invention to form a temporary or semi-permanent bridge is also provided. A typical bridge includes three teeth. Therefore, in preparing a typical bridge using a four-tooth quadrant or anterior shell, a shell segment at one end of the shell is cut off by the dentist to leave a three-segment shell section that covers the missing tooth and the abutment teeth. In a five-tooth embodiment, either two adjacent shell segments at one end of the shell or individual shell segments at each end of the shell, as appropriate, are cut off to leave the desired three-segment shell section.

Regardless of the number of segments in the original shell, however, the selected three-segment shell section consists of integrally-connected shell segments for three consecutive teeth. Once the three-segment section is obtained, it is filled with acrylic resin and mounted in the patient's dentition. Specifically, the end shell segments are emplaced on prepared abutment teeth on opposite sides of a gap in the patient's dentition, with the middle shell of the bridge unit, used to form the pontic, spanning the gap. As the endmost shells are fitted onto the patient's prepared teeth, a portion of the resin extrudes along the gingival margins and from windows at the ends of the shell section to form a good proximal contact with adjacent teeth. The windows can either be partial openings formed in mesio-distal sidewalls of the quadrant shell, or they can be open mesio-distal sides.

With only minor modifications to the above technique, the shells of this invention can also be used to provide a bridge where more than one tooth is missing. If, for example, two adjacent teeth are missing, either the four- or five-segment embodiment of the invention can be used to prepare a bridge. If the four tooth embodiment is used, no cutting of the shell is necessary and the entire shell provides the section used to form the bridge. In the five-segment embodiment, one segment at the appropriate end is removed to leave a four-segment section for forming the bridge. Shells having more than five segments are also contemplated by this invention and could be used in a similar way.

These same shells can also be used by a dentist to provide multi-tooth crowns for adjacent prepared teeth. To provide a multi-tooth temporary or provisional crown, an appropriate multi-tooth shell is selected and sectioned, if necessary, to leave a fused hollow shell section having multiple interconnected shell segments corresponding to just the prepared teeth. This shell section is then filled with resin, placed on the prepared teeth, and left there until the resin has set. Once the resin has set, the resulting unfinished crown is removed from the prepared teeth and adjusted as necessary to fit comfortably within the patient's dentition. The finished multi-tooth crown forms a composite structure is then cemented onto the prepared teeth. As an added benefit of this invention, the remaining, unused shell segments can be saved and used at another time for preparing crowns for teeth corresponding to those unused segments.

BRIEF DESCRIPTION OF THE DRAWINGS

The foregoing and other objects, features and advantages of the invention will become more readily apparent from the following detailed description of preferred embodiments of the invention, proceeding with reference to the accompanying drawings, in which:

FIGS. 8–13 illustrate a method of using the quadrant shell of FIG. 1 to form a temporary or semi-permanent bridge. More specifically:

FIGS. 14–19 illustrate the use of a quadrant shell to provide a temporary or semi-permanent multi-tooth crown. More specifically:

DETAILED DESCRIPTION

Generally, a multi-tooth shell according to this invention is an integrally molded unit having multiple single-tooth shell segments, wherein each segment corresponds to a different tooth. Each segment has an external shape approximating the buccal, lingual, and occlusal anatomy of the corresponding natural human tooth. Each segment also has an interior cavity sized to fit over a prepared tooth and to be filled with resin.

Various different tooth types can be represented by the shell segments in different multi-tooth shells. For a quadrant shell, these tooth types can include cuspids, bicuspids, and molars. For an anterior shell, they can include cuspids, canines, and incisors. For a hybrid quadrant/anterior shell, these shell segments can correspond to any combination of quadrant and anterior teeth in the order normally occurring in a patient's dentition.

Quadrant shells are preferably formed with segments corresponding to four or five individual teeth within a particular quadrant (i.e., lower left, lower right, upper left, or upper right) of a patient's dentition. A four-segment quadrant shell preferably encompasses either two molars and two bicuspids or one molar, two bicuspids, and a cuspid, in the order normally occurring in human dentition. A five-segment quadrant shell preferably comprises one cuspid, two bicuspids, and two molars, also in their normally occurring order.

FIGS. 1–4 are a top plan view, side elevation views, and a bottom plan view, respectively, of a quadrant shell 20 for making a temporary or semi-permanent bridge or multi-tooth crown according to one embodiment of the invention. Specifically, FIGS. 1–4 illustrate the basic concepts of the present invention in a five segment lower left quadrant shell embodiment. Although these figures are specifically directed toward a lower left quadrant shell having segments corresponding to five teeth, the basic concepts disclosed in the following description apply equally to shells for other quadrants and/or anterior regions and for various numbers of teeth.

Referring to FIGS. 1–4, the quadrant shell 20 includes five integrally connected segments 20A–E, with each segment corresponding to a different tooth. In this embodiment, the five shell segments 20A, 20B, 20C, 20D, 20E correspond to a cuspid, a first bicuspid, a second bicuspid, a first molar, and a second molar, respectively. Each shell segment 20A–E includes a top wall 22 having an occlusal surface that replicates the occlusal surface of a natural tooth. A buccal sidewall 24 is connected to the top wall 22 and is spaced apart from a lingual sidewall 26, also connected to the top wall 22.

The shell segments are integrally interconnected along the buccal sidewall 24 and lingual sidewall 26, respectively. The sidewalls are externally indented at locations corresponding to the proximal contacts of natural teeth and together form contiguous undulating sidewalls spanning the proximal contact area. The occlusal walls 22 of adjacent shell segments similarly form a contiguous wall spanning multiple teeth. Mesio-distal sidewalls 28, 30, can also be provided at opposite ends of the shell 20 and are connected to the top walls 22 and the buccal and lingual sidewalls 24, 26, of the shell segments 20A, 20E located on opposite mesio-distal sides of the quadrant shell 20.

Together, the outer surfaces of these walls define the outer contours of the prosthodontic device. Inside, these walls define a central cavity 29 that is shaped to receive acrylic resin and to fit over prepared teeth. A detachable tab 21, for handling the shell 20 during making of the bridge or crown, can also be provided, preferably on either the buccal sidewall 24 or the lingual sidewall 26 near the center of the shell 20.

The lingual sidewall 26 can be made shorter than the buccal sidewall 24 for ease of fitting the gingival margins 25, 27. The mesio-distal sidewalls 28, 30 are preferably shorter occloso-gingivally than both the buccal and lingual sidewalls 24, 26. Each of the mesio-distal sidewalls 28, 30 can also include a mesio-distal window 32, 34 that forms a partial opening in its respective sidewall.

The mesio-distal windows 32, 34 allow the acrylic resin to protrude proximally from the cavity to adjacent teeth when the shell 20 is filled with resin and fitted on prepared teeth. Accordingly, each of the mesio-distal windows 32, 34 is preferably sized large enough to allow resin to protrude therefrom in an amount sufficient to form a good proximal contact with an adjacent tooth. Alternatively, the mesio-distal sidewalls can be entirely open to permit proximal flow of resin to adjacent teeth.

The shell 20 is preferably integrally molded of polycarbonate material, but could also be molded or machined from other polymeric or other types of materials. The preferred material for making the shells 20 of the invention is a 20% fine fiber-glass filled polycarbonate. The material forming shell 20 may also include a radio-opaque substance, such as barium sulfate (BaS), so that it will show up on x-rays. The resin used in the invention is preferably Super-T glass-filled acrylic resin and also preferably contains BaS or some other radio-opaque substance so that it will also appear on x-rays. Furthermore, fine size titanium (Ti) particles or powder can be added to the resin to make the resulting bridge or crown more durable and thereby increase its longevity.

Figure 5:
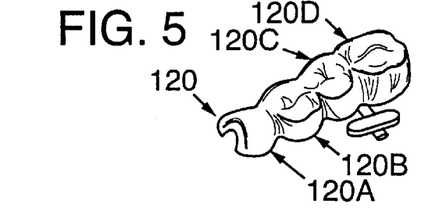
FIG. 5 is a perspective view of a lower left quadrant shell having four shell segments according to a second preferred embodiment of the invention.

Another embodiment of the invention is shown in FIG. 5. Referring to FIG. 5, a quadrant shell 120 according to a second preferred embodiment of the invention includes shell segments 120A–D corresponding to four teeth. In the particular embodiment illustrated, these four teeth include a cuspid, two bicuspids, and a molar, respectively. Another four-segment embodiment could comprise shell segments corresponding to two molars and two bicuspids. The general structure and configuration of this embodiment is otherwise identical to that of the embodiment previously described.

Figure 6:
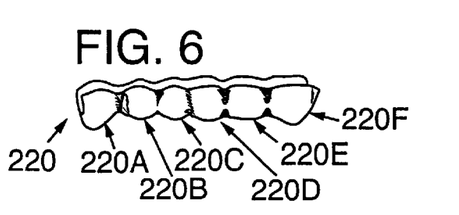
FIG. 6 is a perspective view of an anterior shell according to yet another embodiment of this invention.

Yet another embodiment of the invention is shown in FIG. 6. Referring to FIG. 6, an anterior shell 220 can include a plurality of shell segments 220A–F corresponding to anterior teeth. In the embodiment shown, the anterior shell 220 contains six segments 220A–F corresponding to a canine, a lateral incisor, two central incisors, another lateral incisor, and another canine, respectively. Upper and lower anterior shells of various sizes can be provided and can include shells for various numbers and types of teeth. Three- and five-segment anterior shells, among others, can also be used to provide bridges or crowns according to this invention. The general construction and configuration of this embodiment is similar to those previously described.

Figure 7:
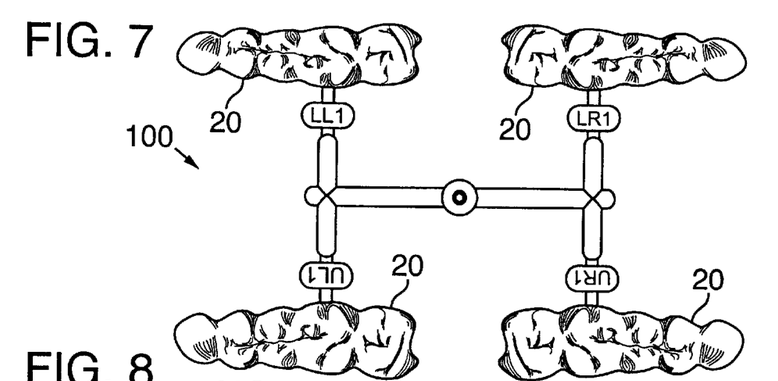
FIG. 7 is a top plan view of a kit according to another aspect of this invention, said kit comprising a plurality of quadrant shells, including two differently sized shells for each quadrant.

A variety of shells 20 of various sizes can be provided to permit selection of a shell that best fits a patient's dentition. FIG. 7 is a top plan view of a set of multi-tooth shells 100 comprising a plurality of quadrant shells 20 according to another aspect of this invention. Referring to FIG. 7, a preferred set of multi-tooth shells 100 has four shells 20 including one shell for each quadrant of the mouth. A kit can be provided having multi-tooth shell sets 100 in various sizes. One kit embodiment, for example, includes both a large and a small sized set of shells 100. The kit therefore provides one large and one small upper right quadrant shell, one large and one small lower right quadrant shell; one large and one small upper left quadrant shell; and one large and one small lower left quadrant shell. Of course, sets and kits can also be made to contain any other selection and combination of multi-tooth shells, as desired.

A typical bridge unit corresponds to three teeth. Accordingly, in preparing a typical bridge using a five-segment shell, two shell segments at one end or individual shell segments at opposite ends are cut off by the dentist to provide a three-segment shell section. Using the alternative four-segment shell embodiment, an appropriately sized shell must be selected. A single-shell segment on an appropriate end is cut off by the dentist to provide the desired three-segment section. In yet another potential embodiment, an appropriate shell could be selected from a plurality of shells each consisting of only three shell segments. Regardless of the embodiment, the selected three-segment shell section should correspond to the missing tooth and the abutment teeth.

Figure 1:
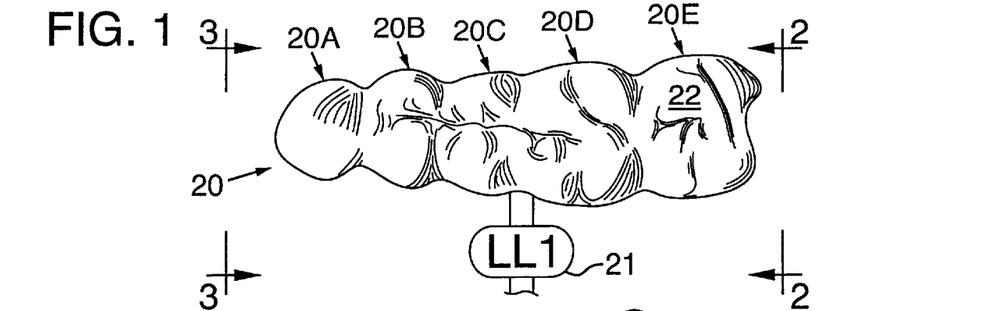
FIG. 1 is a top plan view of a lower left quadrant shell having five shell segments according to a first preferred embodiment of the present invention.
Figure 2:
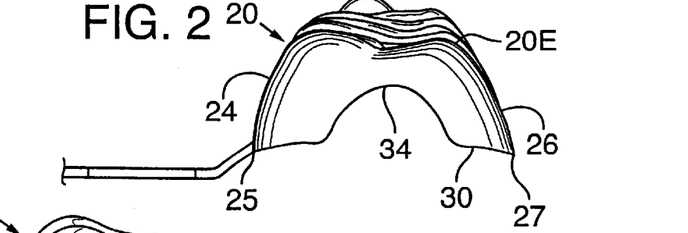
FIG. 2 is a side elevation view showing a mesio-distal side of an end shell segment of the quadrant shell of FIG. 1, the end shell segment corresponding to a molar.
Figure 3:
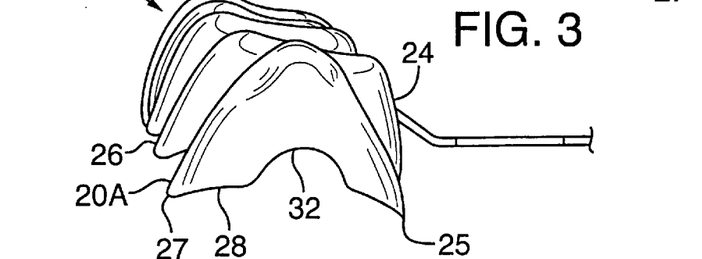
FIG. 3 is a side elevation view showing a mesio-distal side of an opposite end shell segment of the quadrant shell of FIG. 1, the opposite end shell segment corresponding to a cuspid.
Figure 4:
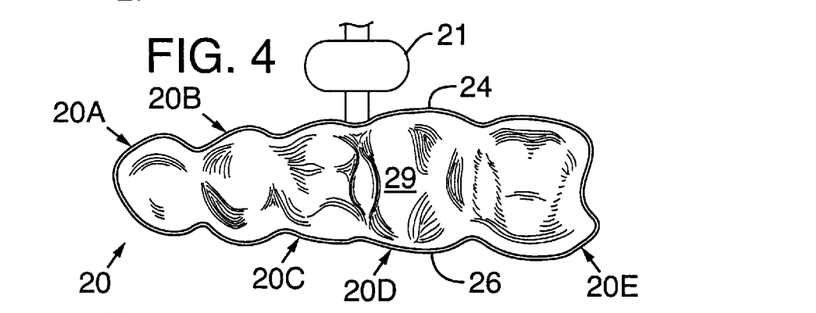
FIG. 4 is a bottom plan view of the quadrant shell of FIG. 1 showing a cavity for receiving resin.
Figures 8, 9, 10:
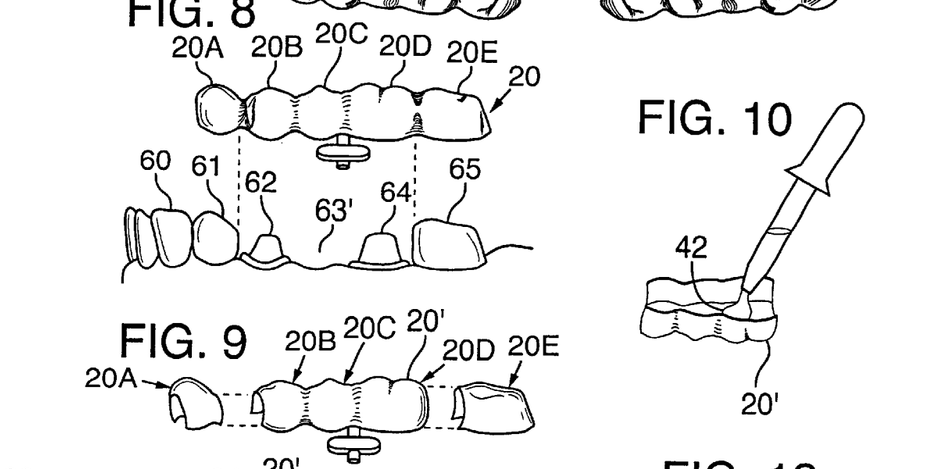
FIG. 8 is a buccal view of a portion of a patient's dentition illustrating the selection of an appropriately sized lower left quadrant shell for use as a temporary or semi-permanent bridge for replacing a missing first molar.
FIG. 9 is a perspective view illustrating sectioning of the selected quadrant shell of FIG. 8 for use as a temporary or semi-permanent bridge for a missing first molar in the lower left quadrant.
FIG. 10 is a perspective view showing filling of the selected section of the quadrant shell of FIG. 9 with a quantity of resin.

FIGS. 8–13 illustrate a method of fabricating a temporary or permanent bridge using a five-segment quadrant shell 20, such as that shown in FIG. 1. Referring to FIGS. 8 and 9, to begin, a dentist selects an appropriate quadrant shell 20 from a plurality of quadrant shells (such as from the set 100 shown in FIG. 7), based on the needs of the particular patient. If, for example, a patient is missing a second bicuspid 63 in the lower left quadrant, an appropriately-sized lower left quadrant shell is selected. The abutment teeth 62, 64 are prepared for crown abutments.

The lower left quadrant shell 20 includes five shell segments 20A, 20B, 20C, 20D, 20E corresponding to five of the patient's teeth 61, 62, 63, 64, 65 respectively. Because only three shell segments are needed, a cutting disc is used to cut off the excess shell segments 20A and 20E by sectioning the shell between segments 20A and 20B and segments 20D and 20E. The remaining three-segment shell section includes segments 20B, 20D corresponding to the abutment teeth 62, 64, and another segment 20C corresponding the missing tooth 63.

Figure 11:
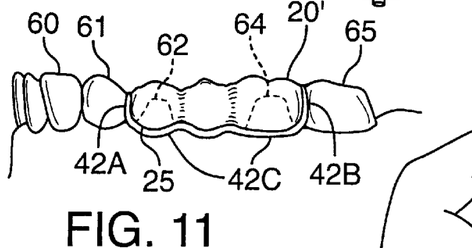
FIG. 11 is a buccal or elevation view illustrating placement of the resin-filled quadrant shell section of FIG. 10 onto abutment teeth and over a gap in the patient's dentition shown in FIG. 8.

Referring to FIGS. 10 and 11, the selected shell section 20', consisting of integrally-connected segments 20B–D corresponding to three consecutive teeth 62, 63, 64, is filled with acrylic resin 42 and mounted in the patient's arch. The end segments 20B, 20D are emplaced on prepared abutment teeth 62, 64 on opposite sides of a gap 63' in the patient's dentition, with the pontic shell segment 20C spanning the gap 63' in the dentition. As the endmost shells 20B, 20D are fitted on the prepared teeth 62, 64, a portion of the resin 42A, 42B extrudes from openings at the ends of the shell section 20' to form proximal contacts with the adjacent teeth 61, 65. Resin 42C also extrudes along the gingival margins 25, 27 near the prepared teeth 62, 64. The acrylic resin 42 in the pontic shell segment 20C does not extrude mesio-distally or gingivally because there is no tooth to obstruct its positioning in that location, but forms to the patient's gum along the gingival margins 25, 27.

Figure 12:
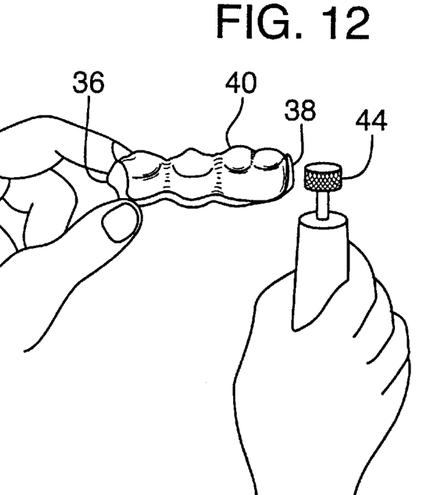
FIG. 12 is a perspective view illustrating adjustment of the bridge formed from the resin-filled shell in FIG. 11 to permit it to fit well both occlusally and gingivally in a patient's dentition.
Figure 13:
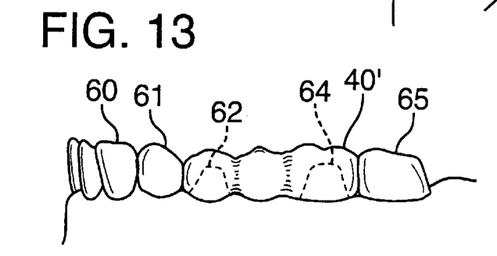
FIG. 13 is a buccal or elevation view illustrating placement of the finished temporary or semi-permanent bridge of FIG. 12 into the patient's dentition shown in FIG. 8.

Referring to FIG. 12, once the resin has sufficiently set, the unfinished bridge 40 is removed, trimmed, and adjusted. The basic method of adjusting the bridge 40 to fit comfortably within the patient's mouth and occlusion generally follows the procedure set forth in applicant's prior patent applications related to crowns. As shown in FIG. 13, once trimmed and fitted, the finished bridge 40' is cemented onto the abutment teeth 62, 64 to provide a temporary or semi-permanent bridge.

As illustrated in FIGS. 14–19, a shell according to this invention can also be used to prepare a multi-tooth crown. For example, referring to FIGS. 14–20, the same lower left quadrant shell 20, that was used in FIGS. 8–13 to form a temporary or semi-permanent bridge, could also be used to temporize a patient's lower left second bicuspid 63 and first molar 64.

Figure 14:
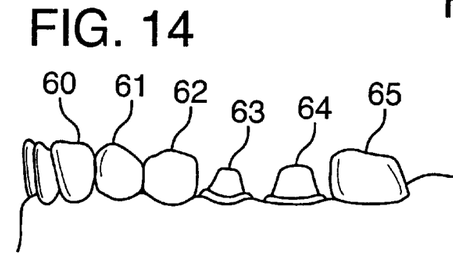
FIG. 14 is a buccal view of a portion of a patient's mouth showing adjacent prepared teeth for receiving a temporary or long-term provisional multi-tooth crown.

FIG. 14 is a perspective view of a portion of a patient's mouth showing adjacent teeth 63, 64 prepared to receiving a temporary or long-term provisional multi-tooth crown. After adjacent teeth 63, 64 are prepared for crowns, an appropriate shell, according to any of the embodiments mentioned above, is selected. In this case, the lower left quadrant shell 20 of FIG. 1 is selected.

Figure 15:
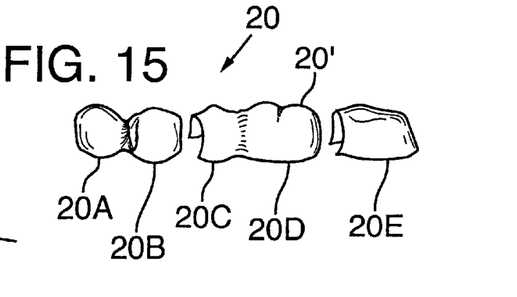
FIG. 15 is a perspective view illustrating the sectioning of a lower left quadrant shell, as shown in FIG. 1, into a desired shell section for forming a multi-tooth crown to fit the prepared teeth of FIG. 14.
Figure 16:
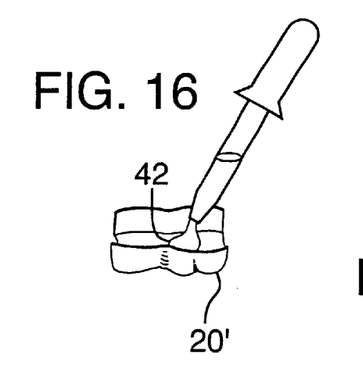
FIG. 16 is a perspective view showing the selected section of FIG. 15 being filled with a quantity of resin.

Referring to FIG. 15, the selected shell 20 is sectioned between the first bicuspid segment 20B and the second bicuspid segment 20C. The shell is also sectioned between the segment 20D corresponding to the first molar 64 and the segment 20E corresponding to the second molar 65. The selected section 20', including fused hollow shell segments 20C, 20D corresponding to the prepared adjacent teeth 63, 64, respectively, is then used to fabricate a temporary multi-tooth crown for both teeth 63, 64. Specifically, referring to FIG. 16, once the adjacent teeth 63, 64 have been prepared for crowns, the selected shell section 20' is filled with a quantity of acrylic resin 42. Trimming the gingival margins 25, 27 of shell section 20', if necessary, should be done before filling it with resin.

Figure 17:
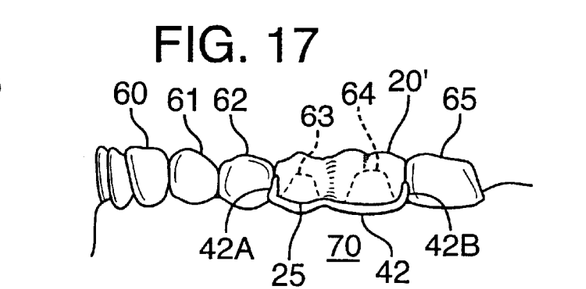
FIG. 17 is a buccal view of a patient's mouth showing emplacement of the resin-filled shell of FIG. 16 onto the prepared teeth of FIG. 14.

The resin-filled shell section 20' is placed on the prepared teeth 63, 64, as illustrated in FIG. 17. The patient then bites down, clamping the resin-filled shell section 20' against opposing teeth. This process establishes an occlusal contact between the occlusal surface 22 of the shell section 20' with the opposing teeth. This step also shapes the resin within the cavity to mate with the prepared teeth 63, 64.

Furthermore, when the patient bites down on the shell section 20', a portion of the resin 42A, 42B is extruded from the cavity through the mesio-distal openings on the opposite mesio-distal sides of section 20', left from the sectioning of the desired section 20' from the rest of the shell. A portion of the resin 42C also extrudes along the gingival margins 25, 27. If an end shell segment 20A, 20E had been part of the selected section 20', resin would be extruded from the window 32, 34 in the mesio-distal sidewall 28, 30. In that case, a portion of the mesio-distal sidewall 28, 30 along the buccal and lingual margins of the mesio-distal window 32, 34 would also direct the extrusion of resin 42A, 42B proximally toward an adjacent tooth.

The resin 42A, 42B extruded from the mesio-distal sides forms mesio-distal protrusions 36, 38 that contact adjacent teeth 62, 65 on proximal sides of the temporary multi-tooth crown 80. If the shell 20 is formed with a lingual sidewall 26 slightly shorter than the buccal sidewall 24, a degree of freedom is provided in positioning the occlusal or top wall 22, as the patient bites down, without the gingival margin 27 of the lingual sidewall 26 engaging the patient's gingiva 70.

Figure 18:
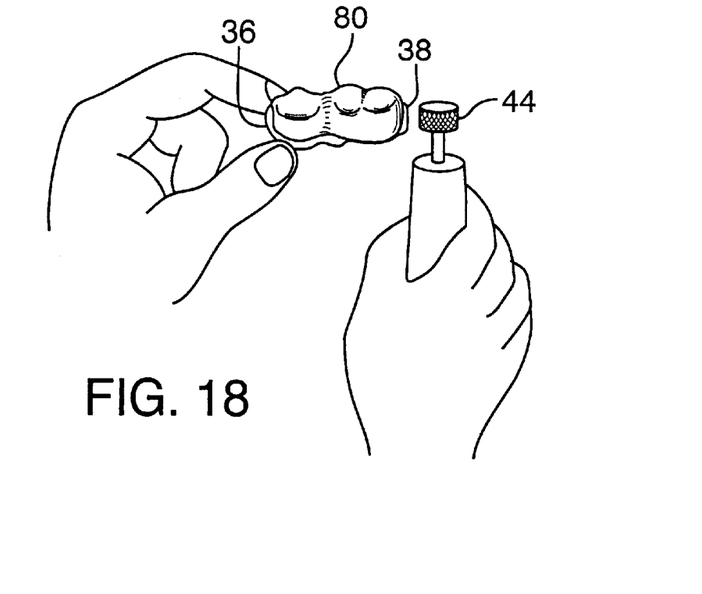
FIG. 18 is a perspective view showing the unshaped temporary crown removed from the patient's mouth for adjustment.

As the resin 42 sets, a chemical reaction bonds the polycarbonate material forming the shell segment 20' and the resin 42 together to form a composite multi-tooth crown 80. Once the resin has sufficiently hardened, the multi-tooth crown 80 is removed and finished. FIG. 18 shows the temporary multi-tooth crown 80 removed from the patient's tooth and held in a dentist's fingers. Referring to FIG. 18, the protrusions 36, 38 of the temporary crown 80 are trimmed and shaped using an acrylic burr 44 to contour the crown's external surface to fit into the patient's dentition occlusally and proximally. The crown can be finished using the burr 44, a disc, and a rubber wheel. The crown 80 may also be tested and ground for bite adjustment to improve its occlusal fit before securing it to the prepared teeth 63, 64.

Figure 19:
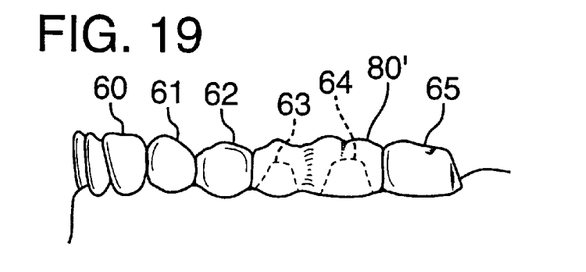
FIG. 19 is a buccal view of a portion of the patient's mouth showing the shaped crown placed back onto the prepared teeth.

FIG. 19 shows the finished temporary crown 80', with shaped extrusions 36, 38, placed back on the patient's prepared teeth 63, 64. The resulting crown 80' is composed of polycarbonate-reinforced acrylic resin. More specifically, the finished crown 80' is a composite crown having a primarily polycarbonate outer layer and an acrylic resin inner layer. The acrylic resin layer also extends from the polycarbonate layer to contact adjacent teeth and to form the gingival margins. The resulting composite polycarbonate and acrylic multi-tooth crown is very durable and provides a good gingival seal. It is therefore suitable for use as a long-term provisional crown as well as a temporary crown.

Once the crown 80' is finished, the border between the shell and filler material is substantially smooth and nearly invisible except upon close inspection. The finished crown 80' is cemented and tightly sealed to the patient's prepared teeth 63, 64 along the gingival margins 25, 27 to secure it within the patient's dentition. The resulting proximal fit to adjacent teeth 62, 65 closely replicates that of a natural tooth, as does the occlusion with opposing teeth.

The multi-tooth crown preparation according to this invention reduces the expense of crown preparation through time and equipment savings. A typical temporary multi-tooth crown (or bridge) according to this invention can be made in about ten minutes. A long-term provisional crown (or bridge) takes just slightly longer. Also, as an added benefit to this invention, the unused shell segment(s) (segments 20A–C corresponding to teeth 60, 61, and 62 in the previous example) can be saved for later use. If the dentist later needs to prepare teeth corresponding to those segments for crowns, he can use the left-over shell segment to produce yet another single or multi-tooth crown.

As a further illustration, if the two lower left bicuspids 61, 62 had instead needed crowns in the first instance, the lower left quadrant shell 20 of FIG. 1 could be used to provide temporization for those teeth. In that case, the remaining unused parts of the bridge shell—including the shell segment 20A corresponding to tooth 60 and the segments 20D, 20E corresponding to molars 63 and 64 could be saved for later use, as needed.

In summary, the quadrant and/or anterior shells of this invention have multiple uses. One use is the temporization of multiple teeth in a single region of the patient's dentition. A second use is to provide a semi-permanent or temporary bridge. The versatility of the design also enables the dentist to use the same multi-tooth shell to repair and/or replace various numbers and configurations of missing teeth.

The lower left quadrant shell 20 of FIG. 1, for example, can be used as a bridge in numerous different situations. If, for instance, the first bicuspid were missing, the first three shell segments 20A–C could be severed from the remaining segments 20D, 20E and used to form a bridge. If, instead, the second bicuspid were missing, the middle three segments 20B–20D could be sectioned from the end segments 20A, 20E and used. Alternatively, if both the second bicuspid and first molar were missing, then the last four shell segments 20B–E could be sectioned from the first segment 20A and used. In this manner, a single shell of this invention can be used as a bridge in many different situations.

That same quadrant shell 20 could likewise be used to temporize teeth in various situations. If, for instance, the first and second bicuspids and first and second molars were all prepared for crowns, shell segments 20B–20E corresponding to those teeth would be sectioned from the remaining shell segment 20A and used to prepare a multi-tooth crown. Similarly, if the second bicuspid and first molar were prepared for crowns, then the two shell segments 20C, 20D corresponding to those teeth would be sectioned off from the remaining segments 20A–B, 20E and used to prepare a multi-tooth crown. In either case, the remaining, unused shell segments could then be saved for future use.

The principals described above with respect to multi-tooth bridges and crowns can also be used in the anterior region or in a combination of anterior and quadrant regions, in a manner similar to that specifically described above. Having described and illustrated the principles of the invention in several preferred embodiments thereof, it should be apparent that the invention can be modified in arrangement and detail without departing from such principles. Various novel features described herein can be used in different combinations and can be modified in shape and dimension without exceeding the scope of the invention. I therefore claim all modifications and variations coming within the spirit and scope of the following claims.

I claim:

1. A multi-tooth shell for making a temporary or semi-permanent bridge or multi-tooth crown, comprising means for recieving a resin such that said shell and resin combined to form said bridge or crown, the means comprising:
    a plurality of integrally-formed and interconnected shell segments, wherein each shell segment has an external shape that corresponds to a different tooth;
    a top wall defining an occlusal surface, said occlusal surface configured to approximate the occlusal surface of natural teeth;
    a buccal sidewall and;
    a lingual sidewall spaced apart from the buccal sidewall; opposite mesio-distal sides, one on each end shell segment; and
    a central cavity defined by inner surfaces of the top wall, buccal sidewall, and lingual sidewall, said cavity configured to receive resin and to fit over prepared teeth.

2. A multi-tooth shell according to claim 1, wherein at least one of the mesio-distal sides comprises a mesio-distal sidewall having a window forming a partial opening in the sidewall for allowing a portion of the resin to protrude from the cavity mesio-distally to an adjacent tooth.

3. A multi-tooth shell according to claim 2, wherein the mesio-distal sidewall is shaped to interfit conformally with a convex mesio-distal surface of an adjacent tooth.

4. A multi-tooth shell according to claim 1, wherein at least one of the mesio-distal sides is completely open to permit proximal resin flow.

5. A multi-tooth shell according to claim 1, wherein the plurality of shell segments correspond to at least one cuspid, at least one bicuspid, and at least one molar.

6. A multi-tooth shell according to claim 1, wherein the shell is a quadrant shell encompassing at least two adjacent teeth.

7. A multi-tooth shell according to claim 1, wherein the shell is an anterior shell for repairing and/or replacing anterior teeth.

8. A multi-tooth shell according to claim 1, wherein said plurality of shell segments comprises at least three shell segments.

9. A multi-tooth shell according to claim 1, wherein said plurality of shell segments comprises four shell segments.

10. A multi-tooth shell according to claim 9, wherein said four shell segments correspond to one cuspid, two bicuspids, and one molar.

11. A multi-tooth shell according to claim 9, wherein said four shell segments correspond to two bicuspids and two molars.

12. A multi-tooth shell according to claim 1, wherein said plurality of shell segments comprises five shell segments.

13. A multi-tooth shell according to claim 1, wherein said five shell segments correspond to one cuspid, two bicuspids, and two molars.

14. A multi-tooth shell according to claim 1, wherein the top wall, the buccal sidewall, and the lingual sidewall of adjacent shell segments form a contiguous shell wall.

15. A set of multi-tooth shells, comprising one or more shells of claim 1 configured to an upper right quandrant shell, a lower right quadrant shell, an upper left quadrant shell, and a lower left quadrant shell.

16. A kit comprising a large-sized set of shells according to claim 15 and a small-sized set of shells according to claim 15.

17. A method of preparing a bridge to replace one or more missing teeth, comprising:
    selecting a multi-tooth shell corresponding to an area of a patient's mouth containing a gap created by one or more missing teeth, the multi-tooth shell having a desired shell section having contiguous buccal, lingual and occalusal walls adapted to cover one or more abutment teeth and the gap;
    filling the desired shell section with a quantity of resin;
    placing the resin-filled shell section into the patient's mouth onto one or more abutment teeth and over the gap;

allowing the resin to at least partially cure to form a bridge before removing the bridge from the patient's mouth;

adjusting the bridge formed by the combination of the shell and resin as necessary to cause it to fit comfortably within the patient's dentition; and securing the adjusted bridge in the patient's mouth.

18. A method according to claim 17 wherein the multi-tooth shell comprises a plurality of shell segments, each corresponding to a different tooth, wherein selecting a multi-tooth shell comprises selecting a shell from among a plurality of shells for an appropriate quadrant or anterior region of the patient's mouth; and further comprising:

sectioning off the desired section comprising segments corresponding to the missing tooth or teeth and the abutment teeth from a remainder of the multi-tooth shell.

19. A method according to claim 17 wherein the multi-tooth shell is a quadrant shell comprising a plurality of shell segments, each segment corresponding to a different tooth in a given quadrant, wherein selecting a multi-tooth shell comprises selecting an appropriately sized quadrant shell corresponding to the quadrant of the patient's mouth containing the missing tooth or teeth, and further comprising:

sectioning off the desired section comprising segments corresponding to the missing tooth or teeth and the abutment teeth from a remainder of the multi-tooth shell.

20. A method according to claim 17, wherein the multi-tooth shell is an anterior shell comprising a plurality of shell segments, each segment corresponding to a different tooth in a given anterior region, wherein selecting a shell comprises selecting an appropriately sized anterior shell corresponding to the anterior region of the patient's mouth containing the missing tooth or teeth, and further comprising:

sectioning off a desired section comprising segments corresponding to the missing tooth or teeth and the abutment teeth from a remainder of the anterior shell.

21. A method according to claim 17, wherein the multi-tooth shell comprises five segments corresponding to a cuspid, two bicuspids, and two molars.

22. A method of preparing a temporary or semi-permanent crown for multiple teeth, comprising:

selecting a multi-tooth shell having a desired shell section corresponding to two or more teeth to be temporized, the shell section including at least two shell segments which form a cavity that is interconnected mesiodistally;

preparing the teeth to be temporized;

filling the desired shell section with a quantity of resin;

placing the resin-filled shell section into the patient's mouth onto the prepared teeth;

allowing the resin to at least partially cure to form a multi-tooth crown before removing the crown from the patient's mouth;

adjusting the crown formed by the combination of the shell and resin as necessary to cause it to fit comfortably within the patient's dentition; and securing the adjusted crown onto the prepared teeth.

23. A method according to claim 22 wherein the multi-tooth shell comprises a plurality of shell segments, each corresponding to a different tooth wherein selecting a multi-tooth shell comprises selecting a shell from among a plurality of shells for an appropriate quadrant or anterior region of the patient's mouth; and further comprising:

sectioning off the desired section comprising segments corresponding to the teeth to be temporized from a remainder of the multi-tooth shell, as necessary, to cover the teeth to be temporized.

24. A method according to claim 22 wherein the multi-tooth shell is a quadrant shell comprising a plurality of shell segments, each segment corresponding to a different tooth in a given quadrant, wherein selecting a shell comprises selecting, from a plurality of quadrant shells, an appropriately sized quadrant shell corresponding to the quadrant of the patient's mouth containing the teeth to be temporized; and further comprising:

sectioning off the desired section comprising segments corresponding to the teeth to be temporized from a remainder of the multi-tooth shell.

25. A method according to claim 22, wherein the multi-tooth shell is an anterior shell comprising a plurality of shell segments, each segment corresponding to a different tooth in a given anterior region, wherein selecting a shell comprises selecting, from a plurality of anterior shells, an appropriately sized anterior shell corresponding to the anterior region of the patient's mouth containing the teeth to be temporized; and further comprising:

sectioning off the desired section comprising segments corresponding teeth to be temporized from a remainder of the anterior shell.

26. A method according to claim 22, wherein the shell comprises five segments corresponding to a cuspid, two bicuspids, and two molars.

27. A method according to claim 22, wherein the shell includes a top wall, a buccal sidewall, and a lingual sidewall interconnected to form a contiguous shell wall.

* * * * *

UNITED STATES PATENT AND TRADEMARK OFFICE
CERTIFICATE OF CORRECTION

PATENT NO. : 6,447,296 B2  
DATED : September 10, 2002  
INVENTOR(S) : Mark L. Worthington It is certified that error appears in the above-identified patent and that said Letters Patent is hereby corrected as shown below:

<u>Title page,</u>
Item [60], Related U.S. Application Data, delete "Provisional application No. 60/190,127, filed on Mar. 16, 2000," and insert
-- This application claims priority from U.S. provisional application No. 60/190,127, filed March 16, 2000, and is a continuation-in-part of application No. 09/484,944, filed January 18, 2000, now U.S. Patent No. 6,257,892, which claimed priority from U.S. provisional application No. 60/131,817, filed April 29, 1999, and which is a continuation-in-part of application No. 09/178,023, filed October 23, 1998, now U.S. Patent No. 6,068,481, which claimed priority from provisional application No. 60/063,410, filed October 18, 1997. --

Signed and Sealed this

Eleventh Day of March, 2003

JAMES E. ROGAN  
*Director of the United States Patent and Trademark Office*